(12) United States Patent
Vergnolle et al.

(10) Patent No.: US 9,125,861 B2
(45) Date of Patent: Sep. 8, 2015

(54) PAR2 AGONISTS FOR USE IN THE TREATMENT OR PREVENTION OF INFLUENZA VIRUS TYPE A INFECTIONS

(75) Inventors: Nathalie Vergnolle, Toulouse Cedex (FR); Beatrice Riteau, Jouy-en-Josas (FR)

(73) Assignees: Institut National de la Sante et de la Recherche Medicale (INSERM), Paris (FR); Institut National de la Recherche Agronomique (INRA), Paris (FR)

( * ) Notice: Subject to any disclaimer, the term of this patent is extended or adjusted under 35 U.S.C. 154(b) by 592 days.

(21) Appl. No.: 13/266,799

(22) PCT Filed: May 3, 2010

(86) PCT No.: PCT/EP2010/055980
§ 371 (c)(1),
(2), (4) Date: Oct. 28, 2011

(87) PCT Pub. No.: WO2010/128016
PCT Pub. Date: Nov. 11, 2010

(65) Prior Publication Data
US 2012/0058127 A1    Mar. 8, 2012

(30) Foreign Application Priority Data

May 4, 2009   (EP) .................................... 09305393

(51) Int. Cl.
*A61K 38/08*    (2006.01)
(52) U.S. Cl.
CPC ...................................... *A61K 38/08* (2013.01)
(58) Field of Classification Search
CPC .................................................... A61K 38/08
See application file for complete search history.

(56) References Cited

U.S. PATENT DOCUMENTS

| | | | |
|---|---|---|---|
| 4,683,202 A | 7/1987 | Mullis | |
| 4,816,397 A | 3/1989 | Boss et al. | |
| 4,861,719 A | 8/1989 | Miller | |
| 4,946,778 A | 8/1990 | Ladner et al. | |
| 5,225,539 A | 7/1993 | Winter | |
| 5,270,163 A | 12/1993 | Gold et al. | |
| 5,278,056 A | 1/1994 | Bank et al. | |
| 5,475,096 A | 12/1995 | Gold et al. | |
| 5,854,033 A | 12/1998 | Lizardi | |
| 5,882,877 A | 3/1999 | Gregory et al. | |
| 6,013,516 A | 1/2000 | Verma et al. | |
| 7,910,556 B2 * | 3/2011 | Ishiwata et al. | ............. 514/21.9 |
| 2006/0165722 A1 * | 7/2006 | De Magistris et al. | .... 424/202.1 |
| 2007/0123508 A1 | 5/2007 | Olsson et al. | |
| 2008/0318960 A1 | 12/2008 | Burstein et al. | |

FOREIGN PATENT DOCUMENTS

| | | | | |
|---|---|---|---|---|
| WO | WO 94/19478 | | 9/1994 | |
| WO | WO 95/14785 | | 6/1995 | |
| WO | WO 96/22378 | | 7/1996 | |
| WO | WO 98/43477 | * | 10/1998 | ............... A01N 1/02 |
| WO | WO 00/15243 | * | 3/2000 | ............. A61K 38/08 |
| WO | WO 03/104268 | | 12/2003 | |

OTHER PUBLICATIONS

Smith et al., 2010, Antivirals for Influenza, Pediatric Drugs, 12(5): 285-299.*
Lee et al., 2012, Targeting the host or the virus: Current and novel concepts for antiviral approaches against influenza virus infection, Antiviral Research, 96: 391-404.*
Lan et al., 2000, Modulation of airway smooth muscle tone by protease activated receptor-1, -2, -3, and -4 in trachea isolated from influenza A virus-infected mice, British Journal of Pharmacology, 129: 63-70.*
Lin et al., 2008, Protease-activated receptor-2 (PAR-2) is a weak enhancer of mucin secretion by human bronchial epithelial cells in vitro, the International Journal of Biochemistry & Cell Biology, 40: 1379-1388.*
Huang, 2007, Protease-activated receptor-1 (PAR1) and PAR2 but not PAR4 mediate relaxations in lower esophageal sphincter, Regulatory Peptides, 142: 37-43.*

* cited by examiner

*Primary Examiner* — Amber D Steele
(74) *Attorney, Agent, or Firm* — Whitham Curtis Christofferson & Cook, PC

(57) ABSTRACT

Methods and compositions (such as pharmaceutical compositions) for treating influenza virus type A infections in human subjects include PAR2 agonists being administered to the subject. The PAR2 agonists include small organic molecules, antibodies, and aptamers. In addition, the PAR2 agonist may be a PAR2 activating peptide. Exemplary PAR2 activating peptides include SLIGRL (SEQ ID NO: 1) and SLIGKV (SEQ ID NO: 2).

13 Claims, No Drawings

```
                      SEQUENCE LISTING

<160> NUMBER OF SEQ ID NOS: 5

<210> SEQ ID NO 1
<211> LENGTH: 6
<212> TYPE: PRT
<213> ORGANISM: Artificial Sequence
<220> FEATURE:
<223> OTHER INFORMATION: Synthetic PAR2 activating peptide

<400> SEQUENCE: 1

Ser Leu Ile Gly Arg Leu
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic PAR2 activating peptide

<400> SEQUENCE: 2

Ser Leu Ile Gly Lys Val
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic control peptide

<400> SEQUENCE: 3

Leu Arg Gly Ile Leu Ser
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic PAR2 activating peptide derivative
<220> FEATURE:
<221> NAME/KEY: MISC_FEATURE
<222> LOCATION: (1)..(1)
<223> OTHER INFORMATION: HOOC-fluoryl at amino terminus
<220> FEATURE:
<221> NAME/KEY: MISC_FEATURE
<222> LOCATION: (5)..(5)
<223> OTHER INFORMATION: carboxy terminus is amidated

<400> SEQUENCE: 4

Leu Ile Gly Arg Leu
1               5
```

```
<210> SEQ ID NO 5
<211> LENGTH: 5
<212> TYPE: PRT
<213> ORGANISM: Artificial Sequence
<220> FEATURE:
<223> OTHER INFORMATION: Synthetic PAR2 activating peptide derivative
<220> FEATURE:
<221> NAME/KEY: MISC_FEATURE
<222> LOCATION: (1)..(1)
<223> OTHER INFORMATION: amino terminus is Z-(CH2)n-CO where Z = an aryl
      group which may or may not have a substituent or a heteroaryl
      group which may or may not have a substituent; n = 0, 1 or 2
<220> FEATURE:
<221> NAME/KEY: MISC_FEATURE
<222> LOCATION: (4)..(4)
<223> OTHER INFORMATION: position 4 is Lys if position 5 is Val or Arg
      if position 5 is Leu
<220> FEATURE:
<221> NAME/KEY: MISC_FEATURE
<222> LOCATION: (5)..(5)
<223> OTHER INFORMATION: position 5 is Val if position 4 is Val or Leu
      if position 4 is Arg

<400> SEQUENCE: 5

Leu Ile Gly Xaa Xaa
1               5
```

PAR2 AGONISTS FOR USE IN THE TREATMENT OR PREVENTION OF INFLUENZA VIRUS TYPE A INFECTIONS

FIELD OF THE INVENTION

The present invention provides methods and compositions (such as pharmaceutical compositions) for treating or preventing influenza virus type A infections.

BACKGROUND OF THE INVENTION

Influenza virus of type A (IAV) causes acute respiratory infections that are highly contagious and afflict humans and animals with significant morbidity and mortality.

Activation of host innate immune system aims at controlling the spreading and deleterious effects of IAV infection. However, excessive inflammatory response, due to a dysregulation of cytokine release and strong recruitment of neutrophils at the site of infection, may also mediate severe lung inflammation and increased pathogenesis of IAV. Cytokine dysregulation during IAV infection is thus often associated with fatal outcome of IAV.

The sites of virus replication in the respiratory tract represent complex microenvironments, in which extracellular proteases are present in large amounts. Some of these proteases (trypsin, tryptase) can play a role both in virus replication and innate immune responses as they are important mediators of inflammatory processes through the activation of a family of receptors called Protease-Activated Receptors (PARs).

To date four PARs, activated by different proteases, have been cloned (PAR1-4). After cleavage of the receptor by proteases, the newly released amino-terminal sequence binds and activates internally the receptor. A role for one member of this family, PAR2, in lung inflammatory processes has been investigated in several studies. On one hand, PAR2 activation by selective agonists in the lung, induces signs of inflammation (recruitment of inflammatory cells, cytokine and chemokine release and endogenous activation of PAR2 promotes allergic sensitization and the recruitment of inflammatory cells to the airways. On the other hand, PAR2 agonists inhibit LPS-induced granulocyte recruitment, and PAR2-deficient mice displayed more severe lung inflammation in a model of bacterial (*Pseudomonas aeruginosa*) infection.

Therefore, the exact role of PAR2 in lung inflammatory response is unclear. Particularly, in the context of viral infection, the role of PAR2 activation still has to be investigated. Elevated PAR levels (including PAR2) have been observed in the airways of IAV-infected mice (Lan R S. et al. 2004), suggesting a role for this receptor in the pathogenesis of viral disease. More recently, an in vitro study has shown that PAR2 activation on monocytes enhanced the suppressive effects of IFN-γ on IAV replication (Feld M. et al. 2008). The role for PAR2 activation on other cell types, and particularly in epithelial cells, one of the primary cell type exposed to different pathogens and to IAV has never been studied in the context of viral infection. Further, the specific role for PAR2 activation in vivo in models of viral infection has never been addressed.

SUMMARY OF THE INVENTION

The invention relates to a PAR2 agonist for use in the treatment or prevention of an influenza virus type A infection.

DETAILED DESCRIPTION OF THE INVENTION

The present invention provides methods and compositions (such as pharmaceutical compositions) for treating or preventing influenza virus type A infections.

The inventors indeed investigated the role of $PAR_2$ in Influenza pathogenesis in vitro and in vivo. In vitro, stimulation of $PAR_2$ on epithelial cells inhibited influenza virus type A (IAV) replication through the production of IFN-γ. In vivo, stimulation of $PAR_2$ using specific agonists protected mice from IAV-induced acute lung injury and death. This effect correlated with an increased clearance of IAV in the lungs associated with an increased IFN-γ production and a decreased presence of neutrophils and RANTES release in bronchoalveolar fluids. More importantly, the protective effect of $PAR_2$ agonist was totally abrogated in IFN-γ-deficient mice. Finally, compared with wild-type mice, $PAR_2$-deficient mice were more susceptible to IAV infection and displayed more severe lung inflammation. In these mice, higher neutrophils counts, increased RANTES concentration but decreased IFN-γ levels were observed in the bronchoalveolar lavages. Collectively, these results showed that $PAR_2$ plays a protective role during IAV infection, through IFN-γ production and decreased excessive recruitment of inflammatory cells to lung alveolae.

Accordingly, a first aspect of the invention relates to a PAR2 agonist for use in the treatment or prevention of an influenza virus type A infection.

As used herein, the term "influenza virus type A infection" refers to any infection caused by an influenza virus type A without consideration of serotype based on hemagglutinine (H1 to H15) and neuraminidase (N1 to N9) expression. Exemplary influenza virus type A that are contemplated by the invention include but are not limited to H1N1, H2N2, H3N2, H5N1, H7N7, H1N2, H9N2, H7N2, H7N3, and H10N7.

In its broadest meaning, the term "treating" or "treatment" refers to reversing, alleviating, inhibiting the progress of influenza virus type A infection. In particular, "prevention" of influenza virus type A infections may refer to the administration of the compounds of the present invention that prevent the symptoms of influenza virus type A infections.

As used herein, the term "PAR2" or "$PAR_2$" has its general meaning in the art and refers to Protease-Activated Receptor-2. The term may include naturally occurring PAR2 and variants and modified forms thereof. The PAR2 can be from any source, but typically is a mammalian (e.g., human and non-human primate) PAR2, particularly a human PAR2.

As used herein the term "PAR2 agonist" is a natural or synthetic compound which binds and activates PAR2 for initiating a pathway signalling and further biological processes. PAR-2 agonistic activity may assessed by various known methods. For example, the Hollenberg's method (Hollenberg, M. D., et al., Can. J. Physiol. Pharmacol., 75,832-841 (1997)), the Kawabata's method (Kawabata, A., et al., J. Pharmacol. Exp. Ther., 288,358-370 (1999)) and the Hawthorne's method (Howthorne et al., A High-Throughput Microtiter Plate-Based Calcium Assay for the Study of Protease-Activated Receptor 2 Activation, Analytical Biochemistry 290, 378-379 (2001)) may be used for assessing a PAR2 agonistic activity.

In one embodiment, a PAR2 agonist according to the invention may be a small organic molecule. The term "small organic molecule" refers to a molecule of a size comparable to those organic molecules generally used in pharmaceuticals. The term excludes biological macromolecules (e. g., proteins, nucleic acids, etc.). Preferred small organic molecules range in size up to about 5000 Da, more preferably up to 2000 Da, and most preferably up to about 1000 Da.

Exemplary PAR2 agonists that are contemplated by the invention include but are not limited to those described in US Patent Application Publications Nos 2007123508 and 2008318960 that are hereby incorporated by reference into the present disclosure. Other examples include those described in Gradell L R et al. 2008, and more particularly AC-55541 [N-[[1-(3-bromo-phenyl)-eth-(E)-ylidene-hydrazinocarbonyl]-(4-oxo-3,4-dihydro-phthalazin-1-yl)-methyl]-benzamide] and AC-264613 [2-oxo-4-phenylpyrrolidine-3-carboxylic acid [1-(3-bromo-phenyl)-(E/Z)-ethylidene]-hydrazide].

In another embodiment, a PAR2 agonist according to the invention is a PAR2 activating peptide that may be HOOC-SLIGRL-NH$_2$ (SEQ ID NO: 1) or HOOC-SLIGKV-NH$_2$ (SEQ ID NO: 2).

In another embodiment a PAR2 agonist of the invention may be a PAR2 activating peptide derivative that may be selected from the group consisting of HOOC-LIGRLO-NH2, HOOC-Fluoryl-LIGRLO-NH2, and trans-cinnamoyl-LIGRLO (tc)-NH2.

Other PAR2 activating peptide derivatives that are contemplated by the invention include those described in International Patent Application Publication No WO03/104268 (that is hereby incorporated by reference into the present disclosure) that are represented by the general formula (I) or a salt thereof:

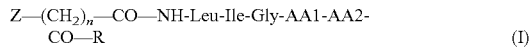

$$Z—(CH_2)_n—CO—NH\text{-Leu-Ile-Gly-AA1-AA2-}CO—R \quad (I)$$

wherein Z represents an aryl group which may or may not have a substituent or a heteroaryl group which may or may not have a substituent; n represents 0, 1 or 2; AA1-AA2 represents Lys-Val or Arg-Leu; and R represents —OH or —NH2.

The aryl group as Z may be a carbon cyclic group of mono-ring type, multi-ring type or condensed ring type, with 6 to 30 carbon atoms, preferably 6 to 14 carbon atoms, specifically including for example phenyl group and naphthyl group, preferably. The heteroaryl group as Z may be a heterocyclic group of 5- to 7-membered mono-ring type, multi-ring type or condensed ring type, the group containing at least one to 3 nitrogen atoms, oxygen atoms or sulfur atoms within the ring and specifically including for example furyl group, thienyl group, pyridyl group or quinolyl group, preferably.

The aryl group or heteroaryl group as Z may or may not have a substituent, which includes but is not limited to any aryl group or heteroaryl group with no adverse effects on the activity of the inventive peptide derivative, specifically including for example a halogen atom, a lower alkyl group, a lower alkoxyl group, phenyl group, a phenyl-lower alkyl group, nitro group, amino group, hydroxyl group, and carboxyl group.

The halogen atom includes for example chlorine atom, fluorine atom, and bromine atom. The lower alkyl group is preferably a linear or branched lower alkyl group with one to 15 carbon atoms, preferably one to 6 carbon atoms, which includes for example methyl group and ethyl group. The lower alkoxyl group preferably includes a linear or branched lower alkoxyl group with one to 15 carbon atoms, preferably one to 6 carbon atoms, which includes for example methoxyl group and ethoxyl group.

The lower alkyl group in the phenyl-lower alkyl group includes alkylene groups including the lower alkyl group, for example methylene group and ethylene group.

Substituents for these lower alkyl group, lower alkoxyl group, phenyl group, and phenyl-lower alkyl group may additionally be substituted with a halogen atom and the like.

The group Z in the general formula (I) in accordance with the invention includes for example substituted or unsubstituted phenyl group, naphthyl group, furyl group, thienyl group, pyridyl group and quinolyl group, specifically including for example phenyl group, 4-methoxyphenyl group, 3-methoxyphenyl group, 2-methoxyphenyl group, 2,4-dimethoxyphenyl group, 3,5-dimethoxyphenyl group, 4-phenethylphenyl group, 3-phenethylphenyl group, 2-phenethylphenyl group, 4-nitrophenyl group, 3-nitrophenyl group, 2-nitrophenyl group, 2,4-dinitrophenyl group, 3,4-dinitrophenyl group, 4-methylphenyl group, 3-methylphenyl group, 2-methylphenyl group, 2,4-dimethylphenyl group, 3,5-dimethylphenyl group, 4-fluorophenyl group, 3-fluorophenyl group, 2-fluorophenyl group, 2,4-difluorophenyl group, 3,5-difluorophenyl group, 2,4,5-trifluorophenyl group, 4-phenylphenyl group, 3-phenylphenyl group, 2-phenylphenyl group, 2-furyl group, 3-furylgroup, 5-methoxy-2-furylgroup, 5-methyl-2-furylgroup, 1-naphthyl group, 2-naphthyl group, 4-methoxy-1-naphthyl group, 4-methyl-1-naphthyl group, 4-methoxy-2-naphthyl group, 4-methyl-2-naphtyl group, 4-pyridyl group, 2-pyridyl group, 3-pyridyl group, 2-methyl-4-pyridyl group, 4-methyl-2-pyridyl group, 2-thienyl group, 3-thienyl group, 3-methyl-2-thienyl group, 4-methyl-2-thienyl group, 4-methyl-3-thienyl group, 6-quinolyl group, 7-quinolyl group, 8-quinolyl group, 4-quinolyl group, 4-methyl-6-quinolyl group and the like.

In the general formula (I), in accordance with the invention, n represents 0, 1 or 2 and the group with the inferior letter "n" is bound to the group Z. When n is 0, the group Z is directly bound to carbonyl group; when n is 1, the group z is bound through methylene group to carbonyl group; and when n is 2, the group Z is bound through ethylene group to carbonyl group.

R in the general formula (I) represents —OH or —NH$_2$, or the salt thereof.

In accordance with the invention, AA1-AA2 in the general formula (I) represents two types of amino acids bound together. The amino acid AA1, is preferably Lys or Arg, while AA2 is preferably Val or Leu. AA1 and AA2 are bound together in the sequence AA1-AA2 along the N-terminal to C-terminal direction. Preferable AA1-AA2 includes Lys-Val or Arg-Leu.

In another embodiment, a PAR2 agonist according to the invention is a protease that is known to activate PAR2. For example, trypsin and tryptase are the principal agonists of PAR2. Trypsin and tryptase cleave PAR2 to expose the tethered ligand SLIGRL (SEQ ID NO: 1) (rat and mouse PAR2), which then binds to conserved regions in extracellular loop II of the cleaved receptor. Certain coagulation factors can also activate PAR2 such as Factor VIIa or Factor Xa. Other examples include protease derived from epithelial cells such as maptriptase, human airway trypsin-like protease, and extra pancreatic tryptic enzymes.

In another embodiment the PAR2 agonist may consist in an antibody (the term including antibody fragment).

In particular, the PAR2 agonist may consist in an antibody directed against the PAR2 in such a way that said antibody activates the receptor.

Antibodies directed against PAR2 can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred. Monoclonal antibodies against PAR2 can be prepared and isolated using any technique that provides for the production of antibody molecules by continuous cell lines in culture. Techniques for production and isolation include but are not limited to the hybridoma technique originally described by Kohler and Milstein (1975); the human B-cell hybridoma technique (Cote et al., 1983); and the EBV-hybridoma technique (Cole et al. 1985). Alternatively, techniques described for the production of single chain antibodies (see, e.g., U.S. Pat. No. 4,946,778) can be adapted to produce anti-PAR2 single chain antibodies. PAR2 agonists useful in practicing the present invention also include anti-PAR2 antibody fragments including but not limited to F(ab')2 fragments, which can be generated by pepsin digestion of an intact antibody molecule, and Fab fragments, which can be generated by reducing the disulfide bridges of the F(ab')2 fragments. Alternatively, Fab and/or scFv expression libraries can be constructed to allow rapid identification of fragments having the desired specificity to PAR2.

Humanized anti-PAR2 antibodies and antibody fragments therefrom can also be prepared according to known techniques. "Humanized antibodies" are forms of non-human (e.g., rodent) chimeric antibodies that contain minimal sequence derived from non-human immunoglobulin. For the most part, humanized antibodies are human immunoglobulins (recipient antibody) in which residues from a hypervariable region (CDRs) of the recipient are replaced by residues from a hypervariable region of a non-human species (donor antibody) such as mouse, rat, rabbit or nonhuman primate having the desired specificity, affinity and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. Methods for making humanized antibodies are described, for example, by Winter (U.S. Pat. No. 5,225,539) and Boss (Celltech, U.S. Pat. No. 4,816,397).

Then after raising antibodies directed against PAR2 as above described, the skilled man in the art can easily select those activating PAR2.

In another embodiment the PAR2 agonist may be an aptamer. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformationally constrained antibody variable region displayed by a platform protein, such as *E. coli* Thioredoxin A that are selected from combinatorial libraries by two hybrid methods (Colas et al., 1996).

Then after raising aptamers directed against PAR2 as above described, the skilled man in the art can easily select those activating PAR2.

A further object of the invention relates a method for screening a PAR2 agonist for use in the treatment or prevention of an influenza virus type A infection.

For example, the screening method may measure the binding of a candidate compound to PAR2, or to cells or membranes bearing PAR2, or a fusion protein thereof by means of a label directly or indirectly associated with the candidate compound. Furthermore, the screening method may involve measuring or, qualitatively or quantitatively, detecting ability of said candidate compound to activate PAR2.

In a particular embodiment, the screening method of the invention comprises the step consisting of:
a) providing a plurality of cells expressing PAR2 on their surface:
b) incubating said cells with a candidate compound;
c) determining whether said candidate compound binds to and activates PAR2; and
d) selecting the candidate compound that binds to and activates PAR2.

In a particular embodiment, the screening method of the invention may further comprising a step consisting of administering the candidate compound selected at step d) to an animal model of influenza virus type A infection to validate the protective effects of said candidate compound.

In general, such screening methods involve providing appropriate cells which express PAR2 on their surface. In particular, a nucleic acid encoding PAR2 may be employed to transfect cells to thereby express the receptor of the invention. Such a transfection may be accomplished by methods well known in the art. In a particular embodiment, said cells may be selected from the group consisting of the mammal cells reported yet to express PAR2 (e.g. epithelial cells).

The screening method of the invention may be employed for determining a PAR2 agonist by contacting such cells with compounds to be screened and determining whether such compound activates PAR2.

According to a one embodiment of the invention, the candidate compounds may be selected from a library of compounds previously synthesised, or a library of compounds for which the structure is determined in a database, or from a library of compounds that have been synthesised de novo or natural compounds. The candidate compound may be selected from the group of (a) proteins or peptides, (b) nucleic acids and (c) organic or chemical compounds (natural or not). Illustratively, libraries of pre-selected candidate nucleic acids may be obtained by performing the SELEX method as described in documents U.S. Pat. No. 5,475,096 and U.S. Pat. No. 5,270,163. Further illustratively, the candidate compound may be selected from the group of antibodies directed against PAR2.

PAR-2 activation with the candidate compound can be tested by various known methods. For example, the Hollenberg's method (Hollenberg, M. D., et al., Can. J. Physiol. Pharmacol., 75, 832-841 (1997)), the Kawabata's method (Kawabata, A., et al., J. Pharmacol. Exp. Ther., 288, 358-370 (1999)) and the Hawthorne's method (Howthorne et al., A High-Throughput Microtiter Plate-Based Calcium Assay for the Study of Protease-Activated Receptor 2 Activation, Analytical Biochemistry 290, 378-379 (2001)) may be used for performing the screening method of the invention.

Another object of the invention relates to a method for treating or preventing a influenza virus type A infection comprising administering a subject in need thereof with an PAR2 agonist.

As used herein, the term "subject" denotes a mammal, such as a pig and a primate. Preferably, a subject according to the invention is a human.

PAR2 agonists may be administered in the form of a pharmaceutical composition, as defined below.

Preferably, the PAR2 agonist of the invention is administered in a therapeutically effective amount. By a "therapeutically effective amount" is meant a sufficient amount the PAR2 agonist according to the invention to treat or prevent influenza virus type A infections at a reasonable benefit/risk ratio applicable to any medical treatment.

It will be understood that the total daily usage of the compounds and compositions of the present invention will be decided by the attending physician within the scope of sound medical judgment. The specific therapeutically effective dose level for any particular patient will depend upon a variety of factors including the deficit being treated and the severity of the deficit; activity of the specific compound employed; the specific composition employed, the age, body weight, general health, sex and diet of the patient; the time of administration, route of administration, and rate of excretion of the specific compound employed; the duration of the treatment; drugs used in combination or coincidential with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

The PAR2 agonist may be combined with pharmaceutically acceptable excipients, and optionally sustained-release matrices, such as biodegradable polymers, to form therapeutic compositions.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

In the pharmaceutical compositions of the present invention, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms. Preferably, the pharmaceutical composition according to the invention is preferably administered in an intranasal administration form.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The PAR2 agonist can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active polypeptides in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

The PAR2 agonist may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds of the invention formulated for parenteral administration, such as intravenous or intramuscular injection, other pharmaceutically acceptable forms include, e.g. tablets or other solids for oral administration; liposomal formulations; time release capsules; and any other form currently used.

Another aspect of the invention relates to a PAR2 agonist for inhibiting replication of an influenza virus type A.

Another aspect of the invention relates to a PAR2 polypeptide for use in the treatment or prevention of influenza virus type A infections.

Another aspect of the invention relates to a nucleic acid molecule encoding for a PAR2 polypeptide for use in the treatment or prevention of influenza virus type A infections.

Typically, said nucleic acid is a DNA or RNA molecule, which may be included in any suitable vector, such as a plasmid, cosmid, episome, artificial chromosome, phage or a viral vector.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence.

So, a further object of the invention relates to a vector comprising a nucleic acid encoding for a PAR2 polypeptide for use in the treatment or prevention of influenza virus type A infections.

Such vectors may comprise regulatory elements, such as a promoter, enhancer, terminator and the like, to cause or direct expression of PAR2 upon administration to a subject. Examples of promoters and enhancers used in the expression vector for animal cell include early promoter and enhancer of SV40 (Mizukami T. et al. 1987), LTR promoter and enhancer of Moloney mouse leukemia virus (Kuwana Y et al. 1987), promoter (Mason J O et al. 1985) and enhancer (Gillies S D et al. 1983) of immunoglobulin H chain and the like.

Any expression vector for animal cell can be used, so long as the nucleic acid encoding for PAR2 can be inserted and expressed. Examples of suitable vectors include pAGE107 (Miyaji H et al. 1990), pAGE103 (Mizukami T et al. 1987), pHSG274 (Brady G et al. 1984), pKCR (O'Hare K et al. 1981), pSG1 beta d2-4-(Miyaji H et al. 1990) and the like. Other examples of plasmids include replicating plasmids comprising an origin of replication, or integrative plasmids, such as for instance pUC, pcDNA, pBR, and the like. Other examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. No. 5,882,877, U.S. Pat. No. 6,013,516, U.S. Pat. No. 4,861,719, U.S. Pat. No. 5,278,056 and WO 94/19478.

A further object of the invention relates to a method of testing whether a subject is predisposed to an influenza virus type A infection, which comprises the step of analyzing a biological sample from said subject for:

(i) detecting the presence of a mutation in the PAR2 gene and/or its associated promoter, and/or (ii) analyzing the expression of the PAR2 gene.

As used herein, the term "biological sample" refers to any sample from a subject such as blood or serum.

Typical techniques for detecting a mutation in the PAR2 gene may include restriction fragment length polymorphism, hybridisation techniques, DNA sequencing, exonuclease reistance, microsequencing, solid phase extension using ddNTPs, extension in solution using ddNTPs, oligonucleotide assays, methods for detecting single nucleotide polymorphism such as dynamic allele-specific hybridisation, ligation chain reaction, mini-sequencing, DNA "chips", allele-specific oligonucleotide hybridisation with single or dual-labelled probes merged with PCR or with molecular beacons, and others.

Analyzing the expression of the PAR2 gene may be assessed by any of a wide variety of well-known methods for detecting expression of a transcribed nucleic acid or translated protein.

In a preferred embodiment, the expression of the PAR2 gene is assessed by analyzing the expression of mRNA transcript or mRNA precursors, such as nascent RNA, of said gene. Said analysis can be assessed by preparing mRNA/cDNA from cells in a biological sample from a subject, and hybridizing the mRNA/cDNA with a reference polynucleotide. The prepared mRNA/cDNA can be used in hybridization or amplification assays that include, but are not limited to, Southern or Northern analyses, polymerase chain reaction analyses, such as quantitative PCR (TaqMan), and probes arrays such as GeneChip™ DNA Arrays (AFFYMETRIX).

Advantageously, the analysis of the expression level of mRNA transcribed from the PAR2 gene involves the process of nucleic acid amplification, e. g., by RT-PCR (the experimental embodiment set forth in U.S. Pat. No. 4,683,202), ligase chain reaction (BARANY, Proc. Natl. Acad. Sci. USA, vol. 88, p: 189-193, 1991), self sustained sequence replication (GUATELLI et al., Proc. Natl. Acad. Sci. USA, vol. 57, p: 1874-1878, 1990), transcriptional amplification system (KWOH et al., 1989, Proc. Natl. Acad. Sci. USA, vol. 86, p: 1173-1177, 1989), Q-Beta Replicase (LIZARDI et al., Biol. Technology, vol. 6, p: 1197, 1988), rolling circle replication (U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

In another preferred embodiment, the expression of the PAR2 gene is assessed by analyzing the expression of the protein translated from said gene. Said analysis can be assessed using an antibody (e.g., a radio-labeled, chromophore-labeled, fluorophore-labeled, or enzyme-labeled antibody), an antibody derivative (e.g., an antibody conjugate with a substrate or with the protein or ligand of a protein of a protein/ligand pair (e.g., biotin-streptavidin)), or an antibody fragment (e.g., a single-chain antibody, an isolated antibody hypervariable domain, etc.) which binds specifically to the protein translated from the PAR2 gene.

Said analysis can be assessed by a variety of techniques well known from one of skill in the art including, but not limited to, enzyme immunoassay (EIA), radioimmunoassay (RIA), Western blot analysis and enzyme linked immunoabsorbent assay (RIA).

The method of the invention may comprise comparing the level of expression of the PAR2 gene in a biological sample from a subject with the normal expression level of said gene in a control. A significantly weaker level of expression of said gene in the biological sample of a subject as compared to the normal expression level is an indication that the patient is predisposed to developing an influenza virus type A infection. The "normal" level of expression of the PAR2 gene is the level of expression of said gene in a biological sample of a subject not afflicted by any influenza virus type A infection. Preferably, said normal level of expression is assessed in a control sample (e.g., sample from a healthy subject, which is not afflicted by any influenza virus type A infection) and preferably, the average expression level of said gene in several control samples.

The invention will be further illustrated by the following figures and examples. However, these examples and figures should not be interpreted in any way as limiting the scope of the present invention.

EXAMPLE 1

Protective Role for Protease-Activated-Receptor-2 Against Influenza Virus Pathogenesis via an Interferon-γ-Dependent Pathway Material & Methods
Virus Strains and Cells:

The human alveolar type II (A549) and the Madin-Darby Canine Kidney cell lines, used in this study, were obtained from the American Type Culture Collection (ATCC, Rockville, Md.) and grown as previously described (LeBouder F. et al. 2008; Riteau B. et al. 2003). The IAV A/PR/8/34 (H1N1), (a gift from G F Rimmelzwaan, Rotterdam, Netherlands) was grown and produced as previously described ((LeBouder F. et al. 2008). $PAR_2$-activating peptide (SLIGRL-$NH_2$) (SEQ ID NO:1) and control peptide (LRGILS-$NH_2$) (SEQ ID NO:3) inactive on $PAR_2$, were synthesized at the protein synthesis facility of the University of Calgary. HPLC chromatography and mass spectrometry were used to assess the purity of the peptides.

RT-PCR Analysis:

A549 cells were infected or not at a multiplicity of infection (MOI) of 1 at different times post-infection. Total RNA were extracted and RT-PCR analysis was done as previously described (Adrian Cabestre F. et al 1999; Rage F. et al. 1999). As a positive control template for $PAR_2$ mRNA, we used a cloned cDNA of human $PAR_2$ (c). Quantification of mRNA modification was done using the Image quant Software.

Flow Cytometry Analysis:

A549 cells were infected or not at a MOI of 0.001 for 24 hours and flow cytometry experiments were done on permeabilized cells, as previously described (Riteau B. et al. 2001; Riteau B. et al. 2001), using the SAM11 anti-$PAR_2$ antibody (Santa-cruz biotechnology, Inc, USA). $PAR_2$ stimulation of A549 cells was performed using 250 μM of $PAR_2$ specific activating peptide SLIGRL-$NH_2$ and flow cytometry experiment was performed 24 hours post-stimulation.

$PAR_2$ Stimulation of A549 Cells:

Cells were stimulated or not for 2 hours with 250 μM of $PAR_2$ specific activating peptide SLIGRL-$NH_2$ or LRGILS-$NH_2$ prior to infection with the IAV A/PR8/34 strain. After the indicated times post-stimulation, the amount of RANTES or IFN-γ released was analyzed in the culture supernatants by ELISA (R&D Systems) Bernard D. et al. 2006; Pascale F. et al. 2008). Virus titers were analyzed by classical plaque assays. For blocking experiments anti-IFN-γ immunoserum or control irrelevant isotypic immunoserum (BD Biosciences, France) were added to A549 culture dishes at a concentration of 20 μg/ml. Pre-incubation of the Ab was performed one hour before infection.

Infection and $PAR_2$ Stimulation of Mice:

Six-weeks-old C57BL/6 female mice were purchased from Charles River Laboratories (Lyon, France) and experiments were undertaken under specific pathogen-free conditions at the INRA animal care facilities (Jouy-en-Josas, France). All animal experiments were carried out under the authority of licence issued by the Direction des Services Vétérinaires (accreditation number 78-114). For the determination of lethal and sublethal dose of IAV infection, mice were anaesthetized and inoculated intranasally with different plaque-forming-unit (pfu) of IAV. For $PAR_2$ stimulation experiments, mice were anaesthetized every day for 3 days. The first day, anaesthetized mice were infected intranasally with 50 000 pfu of A/PR/8/34 in the presence or absence of SLIGRL-$NH_2$ or RLGILS-$NH_2$ at different concentrations (50 μl/mice). Intranasal treatments with SLIGRL-$NH_2$ or the control peptide LRGILS-$NH_2$ were also repeated at days 2 and day 3 after infection. Virus loads were determined by plaque assays 24 and 48 hours post-infection in the lungs of sacrificed mice.

Six-weeks-old IFN-γ-deficient mice (background C57BL/6, n=36) obtained from the INRA "Experimental Infectiology Platform" of Tours (France) were anaesthetized once and infected intranasally with 50 000 pfu of A/PR/8/34 in the presence or absence of SLIGRL-$NH_2$. C57BL/6J/WT mice (n=20) were used as control. Infected mice were then monitored daily for survival.

$PAR_2$-deficient mice and littermates, originally obtained from Johnson & Johnson Research and Development and breeded at the University of Calgary animal care facility, were infected intranasally with 10, 30 or 60 pfu of A/PR/8/34. Infected mice were monitored daily for survival and weight.

May-Grünwald-Giemsa Staining:

Bronchoalveolar lavage fluids (BAL), were collected in PBS (Gibco) supplemented with 1 mM EDTA (Gibco). After cytocentrifugation, percentage of polynuclear neutrophils was determined by counting a total of 500 cells/sample by microscopic examination of May-Grünwald and Giemsa stained cytocentrifuge slides.

Lung Histology:

Lung tissue sections were cut from whole lungs fixed in 10% formalin and embedded in paraffin. Twelve μm thick sections were taken and stained with hematoxylin and eosin for histopathological evaluation as previously describe (Riteau B. et al. 2003).

Statistical Analysis:

The statistical significance of M2 and $PAR_2$ mRNA up regulation in IAV-infected cells was analyzed using a Kruskall-Allis test and a t test. The Mann-Whitney test was used for statistical significance of viral replication, ELISA experiments as well as the quantification of neutrophils in LBA. Kaplan-Meier test was used for survival differences in mice. The statistical significance was noted when necessary and tested with a threshold of $p<0.05$ (*).

Results

Up Regulation of $PAR_2$ in IAV-Infected Cells:

To investigate the role of $PAR_2$ in IAV replication, we first determined the influence of A/PR/8/34 infection on the expression of $PAR_2$ in human alveolar A549 epithelial cells infected or not with IAV. RT-PCR analysis showed that $PAR_2$ mRNA was significantly increased in infected compared to uninfected cells by comparing the levels of $PAR_2$ mRNA to actin mRNA, used as a standard control. The viral matrix M2 mRNA, which was included as a positive control of viral infection was also increased. In addition, cytometry analysis, performed on permeabilized cells indicated that A549 IAV infection was also associated with elevated $PAR_2$ at the level of protein expression compared to uninfected cells. To highlight the increased synthesis of $PAR_2$ after infection, we overlaid the fluorescence intensity of $PAR_2$ binding in infected cells to the uninfected ones. In contrast, stimulation of A549 cells with $PAR_2$ agonist peptide had no effect in our conditions on $PAR_2$ synthesis. We concluded that IAV infection increased the expression of $PAR_2$ in vitro in lung epithelial cells.

Protective Effects for $PAR_2$ Agonist in IAV-Infected Cells:

Since $PAR_2$ expression was increased in IAV infected lung epithelial cells, which are the first target of IAV (LeBouder F. et al. 2008), we next investigated whether $PAR_2$ activation can modulate IAV replication in those cells. For this purpose, A549 alveolar epithelial cells were infected with IAV and stimulated with the selective $PAR_2$ agonist, SLIGRL-$NH_2$ or a control peptide, LRGILS-$NH_2$. When exposed to the $PAR_2$ agonist, IAV-infected cells subsequently produced less virus, compared to cells that were exposed to the control peptide inactive on $PAR_2$. We concluded that $PAR_2$ activation leads to decreased virus production in A549-infected cells.

We then investigated the effects of $PAR_2$ activation on the release of pro-inflammatory cytokines in lung epithelial cells, infected or not with IAV. In uninfected cells, stimulated or not with the selective $PAR_2$ agonist SLIGRL-$NH_2$, basal levels of RANTES and IFN-γ were observed at the limit of detection. Infection of A549 epithelial cells (Infected-treated control) induced RANTES production but had no effect on IFN-γ release. However, stimulation of $PAR_2$ in those cells (Infected-treated SLIGRL) significantly inhibited RANTES from 48 to 72 h after IAV infection, but induced IFN-γ release. Interestingly, IFN-γ release peaked 8 hours post-infection and was transient. Thus, agonist of $PAR_2$ influences cytokine release in A549-IAV infected cells.

Since IFN-γ is a powerful antiviral molecule (Bach E. et al. 1997), we tested whether a link could exist between the induced IFN-γ release and the decreased viral production in A549-infected cells exposed to $PAR_2$ agonist. For this purpose, infected A549 cells, stimulated with $PAR_2$ agonists or control peptides were incubated with an anti-IFNγ neutralizing antibody, or an irrelevant isotypic IgG control antibody. Results showed that inhibition of IAV replication by $PAR_2$ activation could be reversed by masking IFNγ with a neutralizing specific antibody but not by exposure to an isotype control antibody. This clearly demonstrates that $PAR_2$ mediated-inhibition of IAV replication occurs through an IFN-γ-dependent mechanism.

Protection from IAV-Induced Pathogenesis and Death by $PAR_2$ Agonist:

To investigate the role of $PAR_2$ in vivo, we first characterized in infected wild-type animals the time-course of IAV-induced pathogenesis and death in mice. For this purpose, mice were inoculated intranasally with IAV at different pfu per mice. As expected, increasing numbers of pfu resulted in increased mortality of mice. We determined that a dose of 50 000 pfu resulted in 100% mice mortality (lethal dose), while a dose of 60 pfu/mice was sublethal.

We then investigated whether $PAR_2$ agonist treatment could exert a protective effect against IAV-induced infection in vivo. Wild-type mice were infected intranasally with lethal dose of IAV (50 000 pfu) and stimulated or not with different concentrations of $PAR_2$-activating peptide. Results showed that treatments with the $PAR_2$ agonist SLIGRL-$NH_2$ protected mice from death, in a dose-dependent manner, while the control peptide LRGILS-$NH_2$, at the highest dose, had no effect on survival rate. Interestingly, we observed that in mice infected with 500 pfu, the protection conferred by $PAR_2$ agonist treatment was stable, inhibiting mortality until day 12 at least after infection. The protective effect of $PAR_2$ activation on IAV pathogenesis led us to further investigate whether its activation might regulate the replication of IAV in vivo. Viral load was thus evaluated in the lungs of infected mice stimulated with the $PAR_2$ agonist or a control peptide, 24 and 48 hours post-infection. Results showed that infected mice that have been treated with the specific $PAR_2$ agonist had significantly decreased infectious virus load in their lungs compared to infected mice treated with the control peptide. This was also observed at lower doses of IAV infection (ie: 5000 pfu/mice and 500 pfu/mice). Photographic pictures of the lungs of mice were taken to observe their overall integrity. Lungs of medium or control peptide-treated animals appeared severely injured as manifested by redness and hemorrhaged lungs, compared to lungs from $PAR_2$ agonist-treated mice. Finally, histopathologic examination of the lungs revealed IAV-associated lesions in the lungs with alveolar destruction and loss of the integrity of the membrane and massive inflammatory foci from infected mice. In contrast, lack evidence of pathology was observed in the lungs from uninfected or $PAR_2$ agonist-treated animals. We concluded that $PAR_2$ agonist inhibited IAV replication in vivo and protected mice from IAV-induced lungs hemorrhage, pathogenesis and death.

IAV-Induced Cytokine Release In Vivo Modulated by $PAR_2$ Agonist:

We then investigated whether the protective role for $PAR_2$ activation against IAV-induced tissue damage was associated with an inhibition of excessive inflammatory response. Neutrophil recruitment at the site of infection was evaluated in BAL from infected versus non-infected mice, exposed or not to $PAR_2$ agonists. The influx of neutrophils in BAL from mice infected with IAV and treated with the $PAR_2$ agonist, was significantly decreased both at 24- and 48-hours after infection, compared to infected mice treated with the control peptide LRGILS-$NH_2$. However, 48-hours after infection, the number of neutrophils in BAL of IAV-infected mice treated with the $PAR_2$ agonist was significantly increased compared to its level at 24-hours. Thus, $PAR_2$ agonist inhibited but not abolished IAV-recruitment of neutrophils into the lungs.

Since IAV-induced released of cytokines was modified after $PAR_2$ activation in vitro, we then tested whether $PAR_2$ agonist could exert a similar role in vivo. For this purpose, we followed the secretion of RANTES as well as IFN-γ in BAL from infected versus non-infected mice, exposed or not to PAR$_2$ agonists. Naïve mice that have received intranasal administration of the PAR$_2$ agonist showed a three-fold increase in the release of RANTES in their bronchoalveolar lavage fluid (BAL) but no effect was observed on the release of IFN-γ, compared to mice that were treated with the control peptide. Infection of mice with IAV for 12, 24 and 48 hours (infected-treated control) also provoked the release of RANTES, with respectively a three, twenty and seven-fold increase in BAL, compared to uninfected mice. This increase was significantly inhibited by PAR$_2$ agonist treatment, compared to control peptide-treated mice. No significant increase in IFN-γ release was observed after IAV infection in mice treated with the control peptide, compared to non-infected mice. However, at 24 and 48 h after infection, mice treated with the PAR$_2$ agonist showed a significant increase in the release of IFN-γ. Our results showed a concomitant increase in IFN-γ and an inhibition of RANTES release in BAL fluids from infected/PAR$_2$ stimulated mice, compared to infected/control peptide stimulated mice. We concluded that PAR$_2$ agonist modulates IAV-induced cytokine release in vivo.

Protective Role for PAR$_2$ Against IAV Infection:an IFN-γ-Dependent Mechanism:

To investigate the involvement of IFN-γ in the overall protection of mice against IAV-induced pathogenesis and death in vivo by PAR$_2$ agonist, we used IFN-γ-deficient mice. First, we characterized the time-course of IAV-induced pathogenesis and death in IFN-γ-deficient mice. We determined that a dose of 50 000 pfu resulted in 100% mice mortality (lethal dose), which was consistent with previous reports showing no significant differences between wild-type and IFN-γ-deficient mice in response to IAV infection (Graham M et al. 1993). Thus, we used 50 000 pfu/mice to investigate the involvement of IFN-γ in the protective role of PAR$_2$ against IAV infection. Results showed that, in contrast to wild-type mice that were protected by PAR$_2$-activating peptide treatment, in IFN-γ-deficient mice, treatments with the PAR$_2$ agonist did not protect mice from death. Further, PAR$_2$-activating peptide treatment did not modify the kinetic of weight loss after IAV infection of IFN-γ-deficient mice. We concluded that the absence of IFN-γ in mice abolished PAR$_2$-induced protection against IAV-induced pathogenesis and death.

PAR$_2$ Deficiency Increased Susceptibility to IAV Infection, Pathogenesis and Death:

In order to define the role of endogenous activation of PAR$_2$, PAR$_2$-deficient mice and littermates were infected with sub-lethal doses of IAV (10, 30 or 60 pfu/mice), and survival rate as well as weight loss were observed. Results showed no difference in the survival rate of mice infected with 10 pfu/mice. However, using 30 or 60 pfu/mice, survival rates as well as weight loss were decreased in PAR$_2$-deficient mice compared to the wild-type littermates. We concluded that a lack of PAR$_2$ changes the susceptibility of mice after IAV infection at a threshold of 10 pfu/mice. Lungs from PAR$_2$-deficient mice appeared hemorrhagic and damaged compared to lungs from littermates after IAV infection. Altogether, these results further demonstrate a protective role for endogenous PAR$_2$ during influenza infection in mice.

We finally investigated the effect of PAR$_2$ deficiency in modulating IAV-induced inflammation, using PAR$_2$-deficient mice. As an index of cellular inflammation, we measured neutrophils number in the BAL of IAV infected mice at day 10 post-infection. Results show more neutrophils in the BAL from PAR$_2$-deficient mice compared with wild-type mice infected with 30 or 60 pfu/mice. To examine further the inflammatory response associated with PAR$_2$ deficiency, we followed the secretion of RANTES and IFN-γ in BAL from wild-type versus PAR$_2$-deficient mice. Results showed a significant increase in RANTES but decrease in IFN-γ released in BAL after IAV infection with 30 or 60 pfu/mice, compared to wild type mice but not with 10 pfu/mice. Altogether these results indicate that PAR$_2$ naturally protects mice against IAV induced excessive inflammation and death.

REFERENCES

Throughout this application, various references describe the state of the art to which this invention pertains. The disclosures of these references are hereby incorporated by reference into the present disclosure.

Adrian Cabestre, F., P. Moreau, B. Riteau, E. C. Ibrahim, C. Le Danff, J. Dausset, N. Rouas-Freiss, E. D. Carosella, and P. Paul. 1999. HLA-G expression in human melanoma cells: protection from NK cytolysis. J Reprod Immunol. 43:183-193.

Bach, E. A., M. Aguet, and R. D. Schreiber. 1997. The IFN gamma receptor: a paradigm for cytokine receptor signaling. Annu Rev Immunol. 15:563-5691.

Bernard, D., B. Riteau, J. D. Hansen, R. B. Phillips, F. Michel, P. Boudinot, and A. Benmansour. 2006. Costimulatory receptors in a teleost fish: typical CD28, elusive CTLA4. J Immunol. 176:4191-4200.

Chignard, M., and D. Pidard. 2006. Neutrophil and pathogen proteinases versus proteinase-activated receptor-2 lung epithelial cells: more terminators than activators. Am J Respir Cell Mol Biol. 34:394-398.

Feld, M., V. M. Shpacovitch, C. Ehrhardt, C. Kerkhoff, M. D. Hollenberg, N. Vergnolle, S. Ludwig, and M. Steinhoff. 2008. Agonists of proteinase-activated receptor-2 enhance IFN-gamma-inducible effects on human monocytes: role in influenza A infection. J Immunol. 180:6903-6910.

Gardell L R, Ma J N, Seitzberg J G, Knapp A E, Schiffer H H, Tabatabaei A, Davis C N, Owens M, Clemons B, Wong K K, Lund B, Nash N R, Gao Y, Lameh J, Schmelzer K, Olsson R, Burstein E S. Identification and characterization of novel small-molecule protease-activated receptor 2 agonists. J Pharmacol Exp Ther. 2008 December; 327(3):799-808. Epub 2008 Sep. 3

Graham, M. B., D. K. Dalton, D. Giltinan, V. L. Braciale, T. A. Stewart, and T. J. Braciale. 1993. Response to influenza infection in mice with a targeted disruption in the interferon gamma gene. J Exp Med. 178:1725-1732.

Lan, R. S., G. A. Stewart, R. G. Goldie, and P. J. Henry. 2004. Altered expression and in vivo lung function of protease-activated receptors during influenza A virus infection in mice. Am J Physiol Lung Cell Mol Physiol. 286:L388-398.

LeBouder, F., E. Morello, G. F. Rimmelzwaan, F. Bosse, C. Pechoux, B. Delmas, and B. Riteau. 2008. Annexin II incorporated into influenza virus particles supports virus replication by converting plasminogen into plasmin. J Virol. 82:6820-6828.

Pascale, F., V. Contreras, M. Bonneau, A. Courbet, S. Chilmonczyk, C. Bevilacqua, M. Eparaud, V. Niborski, S. Riffault, A. M. Balazuc, E. Foulon, L. Guzylack-Piriou, B. Riteau, J. Hope, N. Bertho, B. Charley, and I. Schwartz-Cornil. 2008. Plasmacytoid dendritic cells migrate in afferent skin lymph. J Immunol. 180:5963-5972.

Rage, F., B. Riteau, G. Alonso, and L. Tapia-Arancibia. 1999. Brain-derived neurotrophic factor and neurotrophin-3 enhance somatostatin gene expression through a likely direct effect on hypothalamic somatostatin neurons. Endocrinology. 140:909-916.

Riteau, B., C. de Vaureix, and F. Lefevre. 2006. Trypsin increases pseudorabies virus production through activation of the ERK signalling pathway. J Gen Virol. 87:1109-1112.

Riteau, B., D. F. Barber, and E. O. Long. 2003. Vav1 phosphorylation is induced by beta2 integrin engagement on natural killer cells upstream of actin cytoskeleton and lipid raft reorganization. J Exp Med. 198:469-474.

Riteau, B., F. Faure, C. Menier, S. Viel, E. D. Carosella, S. Amigorena, and N. Rouas-Freiss. 2003. Exosomes bearing HLA-G are released by melanoma cells. Hum Immunol. 64:1064-1072.

Riteau, B., N. Rouas-Freiss, C. Menier, P. Paul, J. Dausset, and E. D. Carosella. 2001. HLA-G2, -G3, and -G4 isoforms expressed as nonmature cell surface glycoproteins inhibit NK and antigen-specific CTL cytolysis. J Immunol. 166:5018-5026.

Riteau, B., P. Moreau, C. Menier, I. Khalil-Daher, K. Khosrotehrani, R. Bras-Goncalves, P. Paul, J. Dausset, N. Rouas-Freiss, and E. D. Carosella. 2001. Characterization of HLA-G1, -G2, -G3, and -G4 isoforms transfected in a human melanoma cell line. Transplant Proc. 33:2360-2364.

Steinhoff, M., J. Buddenkotte, V. Shpacovitch, A. Rattenholl, C. Moormann, N. Vergnolle, T. A. Luger, and M. D. Hollenberg. 2005. Proteinase-activated receptors: transducers of proteinase-mediated signaling in inflammation and immune response. Endocr Rev. 26:1-43.

The invention claimed is:

1. A method for treating lung inflammation in a human subject having an influenza virus type A infection by decreasing excessive recruitment of inflammatory cells in lung alveolae of said human subject, comprising the step of
administering, to said human subject having lung inflammation caused by influenza virus type A, a pharmaceutical composition comprising, as a principle active ingredient, a synthetic PAR2 agonist, and
a pharmaceutically acceptable carrier;
wherein said step of administering is performed in a manner which causes a decrease of recruitment of inflammatory cells in lung alveolae of said human subject.

2. The method of claim 1, wherein said synthetic PAR2 agonist is selected from the group consisting of small organic molecules, antibodies, and aptamers.

3. The method of claim 1, wherein said synthetic PAR2 agonist is a synthetic PAR2 activating peptide selected from the group consisting of SLIGRL (SEQ ID NO: 1) or SLIGKV (SEQ ID NO: 2).

4. The method of claim 1, wherein said synthetic PAR2 agonist is administered at a dose of 0.01 to 1000 mg per day.

5. The method of claim 4, wherein said dose is 0.01 to 500 mg per day.

6. The method of claim 1, wherein said pharmaceutical composition comprises from 0.01 to 500 mg of said synthetic PAR2 agonist.

7. The method of claim 6, wherein said pharmaceutical composition comprises from 0.01 to 100 mg of said synthetic PAR2 agonist.

8. The method of claim 1, wherein said therapeutically effective amount is from 0.0002 to 20 mg per kg of body weight per day.

9. The method of claim 8, wherein said therapeutically effective amount is from 0.001 to 7 mg per kg of body weight per day.

10. The method of claim 1, wherein said pharmaceutical composition is formulated for parenteral administration.

11. The method of claim 10, wherein said pharmaceutical composition formulated for parenteral administration comprises a dose selected from the group consisting of: 0.0001 to 1.0 milligrams; 0.001 to 0.1 milligrams; 0.1 to 1.0 milligrams and 10 milligrams.

12. A method for treating lung inflammation in a human subject having an influenza virus type A infection, comprising the step of
administering to said human subject a pharmaceutical composition consisting essentially of a therapeutically effective amount of a synthetic PAR2 agonist, and
a pharmaceutically acceptable carrier.

13. A method for treating lung inflammation in a human subject having an influenza virus type A infection by decreasing excessive recruitment of inflammatory cells in lung alveolae of said human subject, comprising the step of
administering, to a human subject having lung inflammation caused by said influenza virus type A infection, a pharmaceutical composition comprising
i) a synthetic PAR2 agonist having the formula $$Z\text{—}(CH_2)n\text{-}CO\text{—}NH\text{-}Leu\text{-}Ile\text{-}Gly\text{-}AA1\text{-}AA2\text{-}CO\text{—}R \quad (I)$$

wherein Z represents an aryl group which may or may not have a substituent or a heteroaryl group which may or may not have a substituent; n represents 0, 1 or 2; AA1-AA2 represents Lys-Val or Arg-Leu; and R represents —OH or —NH2; and
ii) a pharmaceutically acceptable carrier;
wherein said step of administering causes a decrease of recruitment of inflammatory cells in lung alveolae of said human subject.

* * * * *